(12) United States Patent
Mori et al.

(10) Patent No.: US 6,617,444 B1
(45) Date of Patent: Sep. 9, 2003

(54) DINUCLEOTIDE TETRAPHOSPHATE CRYSTALS

(75) Inventors: Kenya Mori, Kurume (JP); Takanori Miyashita, Choshi (JP); Hideaki Maeda, Choshi (JP); Hiroshi Sato, Choshi (JP); Yutaka Noda, Choshi (JP)

(73) Assignee: Yamasa Corporation, Choshi (JP)

( * ) Notice: Subject to any disclaimer, the term of this patent is extended or adjusted under 35 U.S.C. 154(b) by 0 days.

(21) Appl. No.: 09/700,728

(22) PCT Filed: Jun. 30, 2000

(86) PCT No.: PCT/JP00/04336

§ 371 (c)(1),
(2), (4) Date: Nov. 30, 2000

(87) PCT Pub. No.: WO01/02416

PCT Pub. Date: Jan. 11, 2001

(30) Foreign Application Priority Data

Jun. 30, 1999 (JP) ............................................. 11-184950

(51) Int. Cl.[7] .......................... C07H 19/10; A61K 31/70
(52) U.S. Cl. ....................................... 536/26.22; 514/51
(58) Field of Search ........................... 536/26.22; 514/51

(56) References Cited

U.S. PATENT DOCUMENTS

| 5,837,861 A | * 11/1998 | Pendergast et al. | 536/25.6 |
| 5,900,407 A | * 5/1999 | Yerxa et al. | 514/47 |
| 2001/0011079 A1 | * 8/2001 | Yerxa et al. | 514/51 |
| 2001/0031743 A1 | * 10/2001 | Peterson et al. | 514/47 |

FOREIGN PATENT DOCUMENTS

| JP | 07-242685 A | * 9/1995 |
| WO | WO98/34942 A2 | * 8/1998 |
| WO | WO99/05155 A2 | * 2/1999 |
| WO | WO99/61012 A2 | * 12/1999 |
| WO | WO00/20430 A1 | * 4/2000 |
| WO | WO00/39145 A1 | * 7/2000 |
| WO | WO01/02416 A1 | * 1/2001 |

OTHER PUBLICATIONS

Carmen G. Vallejo, et al., DINUCLEOSIDASETETRA-PHOSPHATASE IN RAT LIVER AND *Artemia Salina*, Biochimica Et Biophysica Acta, Amsterdam, NL, vol., 438, No. 1, pp. 304–309, 1976.

* cited by examiner

Primary Examiner—Johann Richter
Assistant Examiner—Eric Crane
(74) Attorney, Agent, or Firm—Oblon, Spivak, McClelland, Maier & Neustadt, P.C.

(57) ABSTRACT

The present invention is directed to crystals of $P^1$-(2'-deoxycytidine 5'-)$P^4$-(uridine 5'-)tetraphosphate (dCP4U) or a salt thereof and to a process for producing the crystals. The present invention also provides a process for producing dCP4U involving reacting uridine 5'-monophosphate (UMP), 2'-deoxycytidine 5'-monophosphate (dCMP), diphenyl phosphorochloridate (DPC), and pyrophosphate (PPi). The crystals of dCP4U obtained through the process according to the present invention have high purity and high stability and no hygroscopicity as compared with a freeze-dried product, and thereby serve as a useful raw material for preparing a pharmaceutical. The process for producing dCP4U according to the present invention permits use of inexpensive UMP as a raw material and realizes high yield. Thus, the process is suitable for large-scale synthesis of dCP4U.

14 Claims, 7 Drawing Sheets

DINUCLEOTIDE TETRAPHOSPHATE CRYSTALS

FIELD OF THE INVENTION

The present invention relates to crystals of $p^1$-(2'-deoxycytidine 5'-)$P^4$-(uridine 5'-)tetraphosphate (dCP4U) or a pharmaceutically acceptable salt thereof (hereinafter may be referred to simply as "dCP4U") which is useful as a therapeutic agent for chronic bronchitis, sinusitis, and the like; a process for producing the crystals; and a process for efficiently producing dCP4U.

BACKGROUND ART dCP4U represented by the following formula (I):

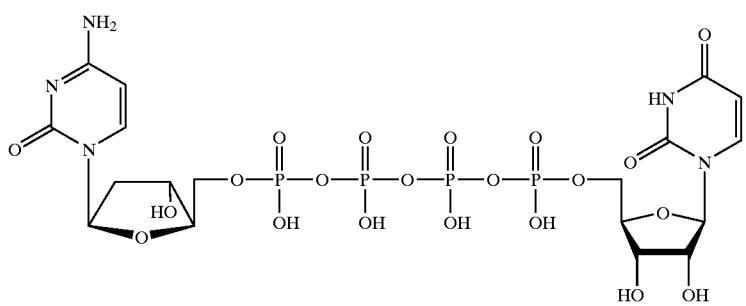

or a salt thereof is a selective agonist to P2Y2 purine receptor and/or P2Y4 purine receptor and is a compound which is expected to be developed as a therapeutic agent for chronic bronchitis, sinusitis, and the like (See WO 98/34942).

Until now, it has not been possible to obtain dCP4U in crystal form, and dCP4U has been prepared only in the form of white powder (white solid) through freeze-drying. The conventionally obtained powdery products of dCP4U have a purity as low as 82% (measured by HPLC). Particularly, it is difficult to separate uridine 5'-triphosphate (UTP) serving as a starting material from dCP4U, and highly purified dCP4U has been produced only with great difficulty through a conventionally employed ion-exchange chromatography (WO 98/34942).

The above white powder of low purity has disadvantages such as hygroscopicity. Therefore, preparation of a pharmaceutical from dCP4U must be carried out in a special apparatus in which moisture is closely controlled. Even after preparation of a pharmaceutical, the product must be tightly packaged. In addition, since the pharmaceutical has a very short available period due to poor stability of the powder product, obtaining highly purified and stable crystals of dCP4U has been desired. dCP4U is synthesized from 2'-deoxycytidine 5'-monophosphate (dCMP) and UTP by use of an activating agent such as dicyclohexylcarbodiimide (DCC). However, conventional processes provide a considerably low synthetic yield; i.e., as low as approximately 9 wt. % (see Example 20 of WO 98/34942), and can never serve as a practical process. Accordingly, development of a process for producing dCP4U at high yield and on a large scale has also been desired.

In view of the foregoing, an object of the present invention is to provide stable crystals of dCP4U which is suitable for preparing drugs. Another object of the invention is to provide a process for producing the crystals. Still another object of the invention is to provide an efficient process suitable for large scale production of dCP4U.

DISCLOSURE OF THE INVENTION

The present inventors have conducted intensive studies on stabilization of dCP4U, and have found that dCP4U having a purity of 95% or more can be prepared through anion exchange chromatography in combination with chromatography employing activated charcoal (activated-charcoal chromatography) and that dCP4U crystals can be produced from such highly-purified dCP4U. The thus-obtained dCP4U crystals have proven to possess a purity considerably higher than that of conventionally produced dCP4U powder, no hygroscopicity and high stability.

The inventors have also conducted intensive studies on methods for synthesizing dCP4U by use of inexpensive uridine 5'-monophosphate (UMP) instead of expensive UTP, and have found that dCP4U can be effectively produced by use of diphenyl phosphorochloridate (DPC) and a pyrophosphate (PPi). The present invention has been accomplished on the basis of these findings.

Accordingly, the present invention provides crystals of dCP4U.

The present invention also provides a process for producing crystals of dCP4U, which process comprises purifying crude dCP4U through anion exchange chromatography and activated-charcoal chromatography and adding a hydrophilic organic solvent to a solution of purified dCP4U, to thereby precipitate dCP4U in the form of crystals.

The present invention also provides a process for producing dCP4U which comprises reacting UMP, dCMP, DPC, and PPi.

BEST MODE FOR CARRYING OUT THE INVENTION

Figure 1:
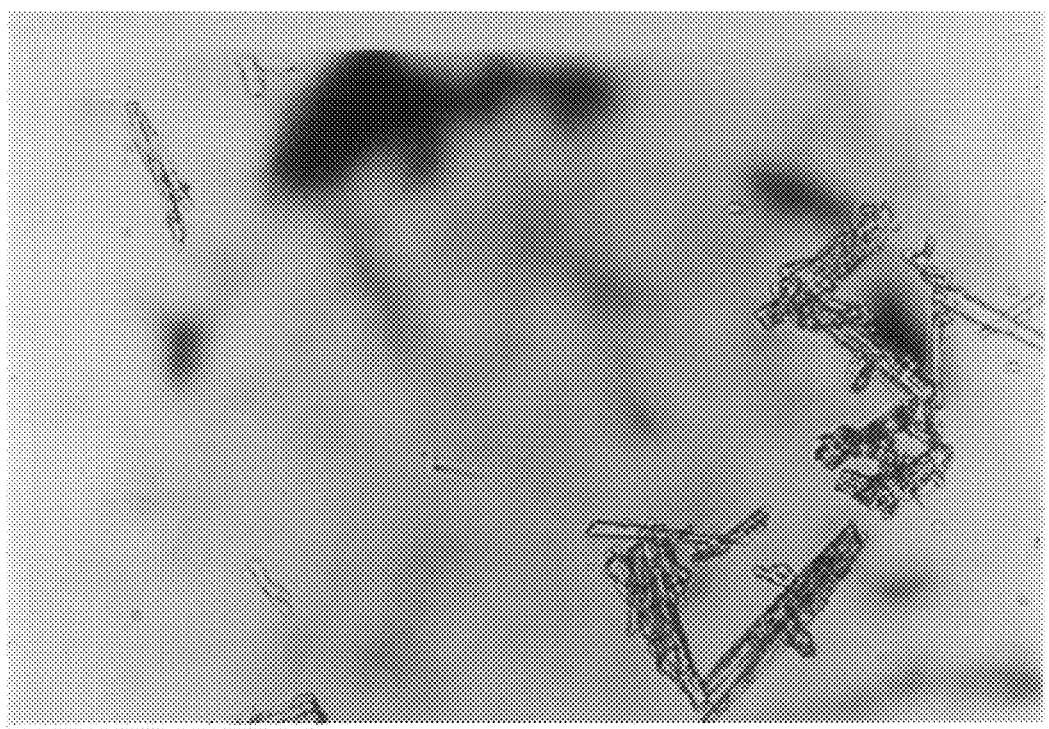
FIG. 1 is a photograph showing crystal form of crystalline dCP4U.4Na (3.5-hydrate). The photograph was taken under a polarizing microscope (magnification: ×440), wherein 1 mm in the image corresponds to 25 μm.

The crystals of dCP4U of the present invention are obtained through purification of crude dCP4U by use of specific means, and addition of a hydrophilic organic solvent to a solution of purified dCP4U, to thereby precipitate dCP4U as crystals. The present invention will next be described in relation to (1) purification of dCP4U and (2) crystallization of dCP4U.

(1) Purification of dCP4U dCP4U can be purified through anion exchange chromatography in combination with activated-charcoal chromatography. Although the two chromatography techniques may be performed in arbitrary sequence, anion exchange chromatography preferably precedes activated-charcoal chromatography, in view of improvement of the purity of dCP4U.

A styrenic or acrylic resin may be used as an anion-exchanging resin in the above-described chromatography techniques. Examples of resins which may be used include strongly basic anion-exchanging resins such as AMBER-LITE IRA 402 (Rohm & Haas Co.), DIAION PA-312, and DIAION SA-11A (Mitsubishi Chemical Co. Ltd.), and weakly basic anion-exchanging resins such as AMBERLITE IRA 67 (Rohm & Haas Co.) and DIAION WA-30 (Mitsubishi Chemical Co. Ltd.).

The activated charcoal may be in the form of chromatography-grade activated charcoal which is crushed or shaped into particles, and may include commercially available products (e.g., those of Wako Pure Chemical Industries, Ltd. and Futamura Chemical Industries, Co., Ltd.).

Chromatography may be carried out in a batch manner, by use of a column, etc. When column chromatography is carried out, an aqueous acid solution or a mixture thereof with a salt having enhanced ionic strength, such as sodium chloride, may be used as an eluent for anion exchange chromatography; and water or an aqueous solution of an alkali such as sodium hydroxide may be used as an eluent for activated-charcoal column chromatography. A small-scale preliminary test may be conducted in order to select the appropriate concentration of each eluent from within the range of 0.001 M to 10 M.

(2) Crystallization of dCP4U dCP4U is crystallized through addition of a hydrophilic organic solvent to a solution containing the thus-purified dCP4U.

Examples of hydrophilic organic solvents which may be used include alcohols having six or fewer carbon atoms, such as methanol and ethanol; ketones such as acetone; ethers such as dioxane; nitriles such as acetonitrile; and amides such as dimethylformamide. Of these, alcohols, especially ethanol, are particularly preferred.

More specifically, a solution of the thus-purified dCP4U, or a slurry obtained through concentration of the solution, is optionally treated to thereby adjust the pH to 5–10, preferably 6–9, and a hydrophilic organic solvent is added to the solution or slurry at 60° C. or lower, preferably 20° C. or lower, to thereby precipitate the solute as stable crystals of dCP4U.

The thus-obtained dCP4U crystals of the present invention contain dCP4U in an amount of 95% or more and UTP in an amount of 3% or less. Preferably, dCP4U crystals contain dCP4U in an amount of 97% or more, and UTP in an amount of 2% or less. More preferably, dCP4U crystals contain dCP4U in an amount of 98% or more, and UTP in an amount of 1% or less.

Such high-purity dCP4U crystals may be in the form of a salt, hydrate, or hydrate salt. Examples of the salts include pharmaceutically acceptable salts such as alkali metal salts such as sodium salts and potassium salts; alkaline earth metal salts such as calcium salts and magnesium salts; and ammonium salts. The dCP4U may be substituted with 1–4 metal atoms to form a salt.

The above hydrate may comprise 1–14 molecules of water which are bound to or adhere to one molecule of dCP4U, and the above hydrate salt may comprise 1–14 molecules of water which are bound to or adhere to one molecule of an alkali metal salt of dCP4U.

Furthermore, the crystals of dCP4U according to the present invention also include tautomers thereof.

The thus-obtained crystals of dCP4U are optionally dried through a customary method such as drying under reduced pressure, drying under air-flow, or drying by heating, and are subsequently placed in a container (e.g., bottle, pouch, can, ampoule). Packing in the container may be achieved so that the container is open, closed, airtight, or sealed. The open-to-air state packing is not preferred, in view of maintenance of storage stability of the crystals.

The process for producing dCP4U according to the present invention comprises reacting UMP, dCMP, DPC, and PPi.

Specifically, the process comprises reacting UMP with DPC to thereby synthesize UMP diphenylphosphate (UMP-DPP); further treating the UMP-DPP-containing reaction mixture with PPi to thereby form UTP in the mixture; and reacting the thus-formed UTP, without isolating from the reaction mixture, with dCMP in the presence of DPC, to thereby form the target dCP4U.

In synthesis of UMP-DPP from UMP, a routinely prepared UMP trialkylamine salt (e.g., UMP tributylamine salt) may be dissolved in a solvent. Examples of the solvents include amides such as DMF and dimethylacetamide (DMAC); cyclic ethers such as dioxane and tetrahydrofuran; ketones such as acetone; and dimethylimidazolidinone, hexamethylphosphoric triamide, or a mixture of two or more of these. Subsequently, DPC and optional trialkylamine are added to the solution, and the mixture is allowed to react at 10–50° C. for approximately 30 minutes to five hours.

The PPis which react with UMP-DPP are preferably PPi-organic alkali salts. Examples of the salts include a hexylamine salt, a dibutylamine salt, a triethylamine salt, and a tributylamine salt.

In the reaction of UMP-DPP with a PPi-organic alkali salt, the PPi-organic alkali salt may be dissolved in a solvent. Examples of such solvents include amides such as DMF, DMAC, and formamide; cyclic ethers such as dioxane and tetrahydrofuran; ketones such as acetone; and dimethylimidazolidinone, hexamethylphosphoric triamide, dimethylsulfoxide, acetonitrile, or a mixture of two or more of these. Subsequently, the solution is added to the thus-synthesized UMP-DPP solution, and the mixture is allowed to react at 10–50° C. for approximately 30 minutes to five hours.

The reaction between UMP-DPP and PPi-organic alkali salt may be carried out in the presence of an adequate base. Examples of the bases include pyridine bases such as pyridine, 2,6-lutidine, 2,4-lutidine, α-picoline, β-picoline, γ-picoline, 2,4-dimethylaminopyridine, α-collidine, β-collidine, and γ-collidine, with pyridine being particularly preferred. A basic solvent for the reaction is also included in the bases used in the present invention. The concentration of the base is not particularly limited. The base is preferably added in an amount of 6 equivalents or more based on UMP, more preferably 18 equivalents or more.

Through the reaction between UMP-DPP and PPi-organic alkali salt, UTP is synthesized in the reaction mixture. The thus-formed UTP and dCMP are reacted in the presence of DPC, to thereby synthesize dCP4U.

Although dCMP per se may be added to the reaction mixture, dCMP is converted into dCMP diphenylphosphate (dCMP-DPP) in a manner similar to that employed in the case of UMP, and the dCMP-DPP may also be added.

The reaction of dCP4U may be carried out by adding, to the aforementioned synthesized UTP solution, DPC in an amount of 1.1 equivalents or more and dCMP or dCMP-DPP in an amount of 0.5–1.5 equivalents based on UMP employed as a starting material, and the mixture is allowed to react at 10–50° C. for approximately 30 minutes to five hours.

The thus-obtained dCP4U is purified and crystallized in the aforementioned manner, to thereby obtain the dCP4U crystals of the present invention.

EXAMPLES

The present invention will next be described in more detail by way of examples, which should not be construed as limiting the invention thereto.

Example 1

Production of dCP4U.4Na Crystals (1) Method using DCC dCP4U was prepared through a routine method as described in WO 98/34942 by use of UTP, dCMP, and DCC. Reaction was carried out on a scale of 20 mmol.

The thus-obtained dCP4U solution was diluted with water to thereby adjust the overall volume to 1,000 ml, and the diluted solution was applied to a column charged with medium basic anion-exchanging resin (AMBERLITE IRA-67, product of Rohm & Haas Co.). Elution was carried out sequentially by use of water, a 0.18 M aqueous hydrochloric acid solution, and a 0.005 M aqueous hydrochloric acid solution containing 0.5 M sodium chloride, thereby collecting fractions containing dCP4U.

The thus-obtained dCP4U fractions (4000 ml) were applied to a column charged with chromatography-grade activated charcoal (Taiko Granular Activated Charcoal SGP, product of Futamura Chemical Industries, Co., Ltd.), and dCP4U was eluted by use of a 0.05 M aqueous sodium hydroxide solution (8000 ml).

The thus-obtained fractions of dCP4U were combined and concentrated, to thereby prepare a slurry. The pH of the slurry was adjusted to 6.0. The slurry was stirred while ethanol was gradually added to the slurry, and the resultant slurry was further cooled to 10° C. with stirring, thereby precipitating dCP4U.4Na crystals. The crystals were separated to thereby yield 8.9 g of dCP4U.4Na crystals. The isolated crystals were dried under reduced pressure at approximately 60° C. for approximately four hours and were then subjected to instrumental analyses.

(2) Method Using DPC

UTP.3Na (12.8 kg) was dissolved in water (135 L), and the resultant solution was applied to a column charged with cation-exchanging resin (product of Mitsubishi Chemical Co. Ltd.). The solution that had passed through the column and fractions which had been eluted with water were combined, and tributylamine (TBA; 13.6 kg) was gradually added to the combined solution with stirring for neutralization. The solution was concentrated, and formamide (10 kg) was added to the solution. The resultant solution was dehydrated by boiling with dioxane. Subsequently, the dehydrated matter was diluted with pyridine (11.6 kg), to thereby prepare a pyridine solution of UTP.

To another tank containing methanol (18 L), dCMP (7.5 kg) was added. TBA (4.5 kg) was gradually added to the solution with stirring, the solution was heated to 60° C. After the ingredients were dissolved, the solution was concentrated to dryness. The dried matter was further dried under vacuum at 75° C. and crushed. The crushed matter (10.3 kg) was suspended into dimethylacetamide (DMAC) (16.7 kg), and diphenyl phosphorochloridate (DPC) (4.4 kg) was added to the suspension, and the mixture was stirred for 10 minutes. Subsequently, TBA (10.8 kg) was further added to the mixture, and the resultant mixture was stirred for 30 minutes, to thereby prepare a dCMP-DPP solution.

To the thus-prepared dCMP-DPP solution, the pyridine solution of UTP which had been prepared in the aforementioned manner was added with stirring. After completion of addition, the mixture was stirred at room temperature overnight, and reaction was terminated by adding deionized water.

To the above mixture, a 30% aqueous sodium hydroxide solution (31 L) was added. The mixture was stirred for 30 minutes, and released TBA was removed through partition. A 6 mol/L hydrochloric acid solution was added to the aqueous layer, to thereby adjust the solution pH to approximately 7. The solution was concentrated through removal of the solvent, and an equivolume of 95% ethanol was added to the concentrated solution. The resultant mixture was allowed to stand overnight. The upper layer of the mixture, i.e., an ethanol layer, was removed through suction, and water was added to the resultant sticky precipitates to thereby dissolve the precipitates. The residual solvent was removed through concentration of the solvent.

The overall volume of the thus-synthesized dCP4U solution was adjusted to 2,500 L, and the solution was applied to a column charged with medium basic anion-exchanging resin (AMBERLITE IRA-97, product of Rohm & Haas Co.). Elution was carried out sequentially with water, a 0.1 mol/L aqueous hydrochloric acid solution, and a 0.005 mol/L aqueous hydrochloric acid solution containing 0.4 mol/L sodium chloride, thereby collecting fractions containing dCP4U.

The thus-obtained dCP4U fractions (2100 L) were applied to a column charged with chromatography-grade activated charcoal (Taiko Granular Activated Carbon SGP, product of Futamura Chemical Industries, Co., Ltd.), and dCP4U was eluted by use of a 0.05 mol/L aqueous sodium hydroxide solution (1200 L).

The thus-obtained fractions were combined and concentrated. The pH of the resultant solution was adjusted to 7.5 by use of a 30% aqueous sodium hydroxide solution. The solution was stirred while 95% ethanol was gradually added to the solution, thereby precipitating dCP4U.4Na crystals. The crystals were separated and dried at 60° C. for four hours, to thereby yield 4.2 kg of dCP4U.4Na crystals (water content: 5.9%, isolation yield: 22%).

>Physical properties of dCP4U.4Na crystals>

The dCP4U.4Na crystals prepared in (1) or (2) of Example 1 and white powder of dCP4U.4Na (freeze-dried product) which was prepared in the same way as in the method described in Example 20 of WO 98/34942 were subjected to instrumental analysis. The crystals were compared with the freeze-dried product in terms of physical properties.

(3) Instrumental Analysis

1) Analysis of Purity

The dCP4U.4Na crystals obtained in (1) and (2) of Example 1, and dCP4U fractions after purification through each chromatography were subjected to analysis of purity by means of high performance liquid chromatography. The results are shown in Tables 1 and 2. Conditions for high performance liquid chromatography are described below.

Column: HITACHIGEL #3013-N (product of Hitachi Keisokuki Service)

Eluent: 10% $CH_3CN$, 0.18 M $NH_4Cl$, 0.03 M $KH_2PO_4$, and 0.03 M $K_2HPO_4$

Detection method: UV detection at 262 nm

TABLE 1

(DCC method)

|  | dCP4U content (%) | UTP content (%) |
|---|---|---|
| Reaction mixture | 55.0 | 28.6 |
| After IE* chromatography | (-) | (-) |
| After AC* chromatography | 97.4 | 0.4 |
| After crystallization | 98.3 | 0.4 |

(-): Not measured, *): IE: Ion exchange, AC: Activated-charcoal

TABLE 2

(DPC method)

|  | dCP4U content (%) | UTP content (%) |
|---|---|---|
| Reaction mixture | (-) | (-) |
| After IE* chromatography | 68.6 | 27.2 |
| After AC* chromatography | 92.8 | 1.5 |
| After crystallization | 98.3 | 0.3 |

(-): Not measured, *): IE: Ion-exchange, AC: Activated-charcoal

2) Crystal Form

FIG. 1 shows a photograph of a typical crystal form of dCP4U.4Na (3.5-hydrate) crystals.

3) Water Content

Water content of the dCP4U.4Na crystals was measured by the Karl Fischer method. The dCP4U.4Na crystals were found to be stabilized at the water content from 6.9 to 17.4 wt. %, which varied in accordance with the degree of drying. The calculation results apparently show that 3.5–10 water molecules bind or adhere to one dCP4U molecule.

4) Melting Point

The melting point of dCP4U.4Na crystals was measured by a conventional method. The melting point was found to be 202–210° C. The melting point of the freeze-dried product was about 195–210° C.

5) X-ray Diffraction

Figure 2:
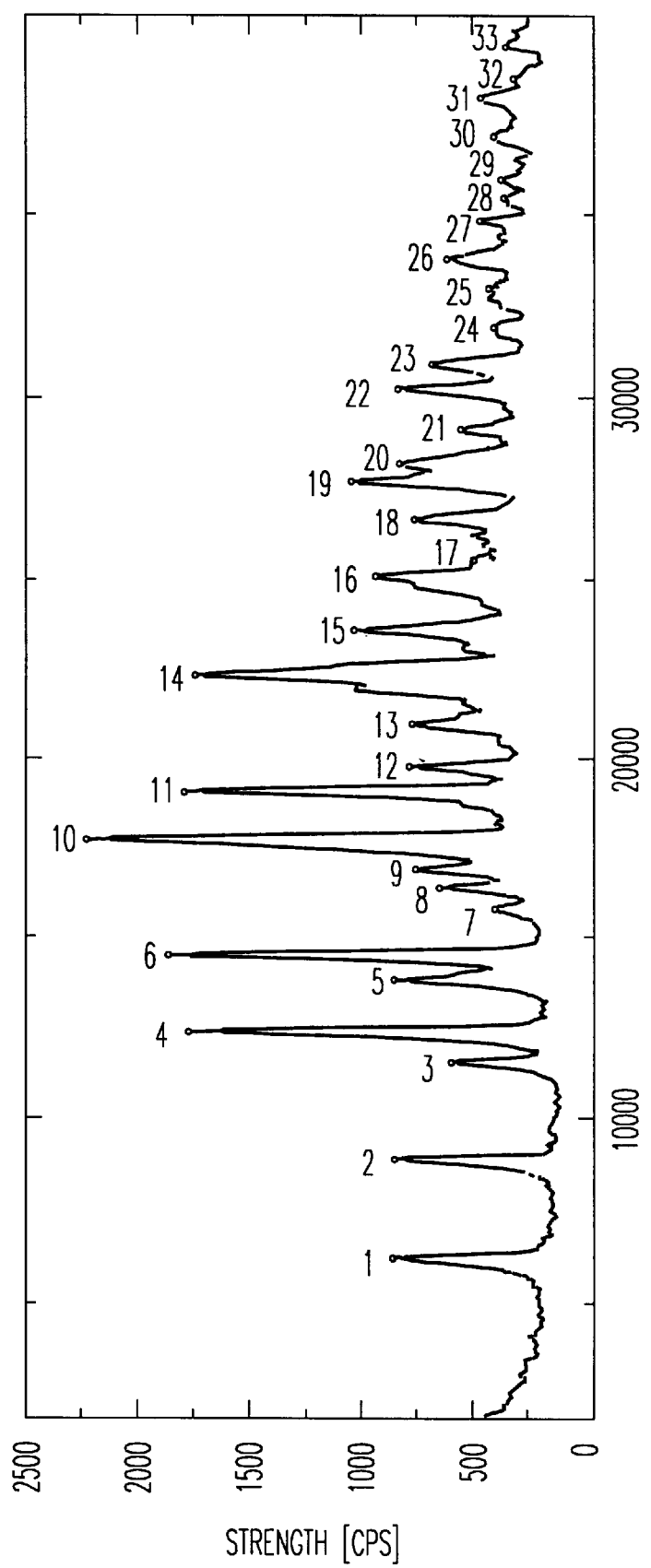
FIG. 2 shows an X-ray diffraction spectrum of crystalline dCP4U.4Na (3.5-hydrate).
Figure 3:
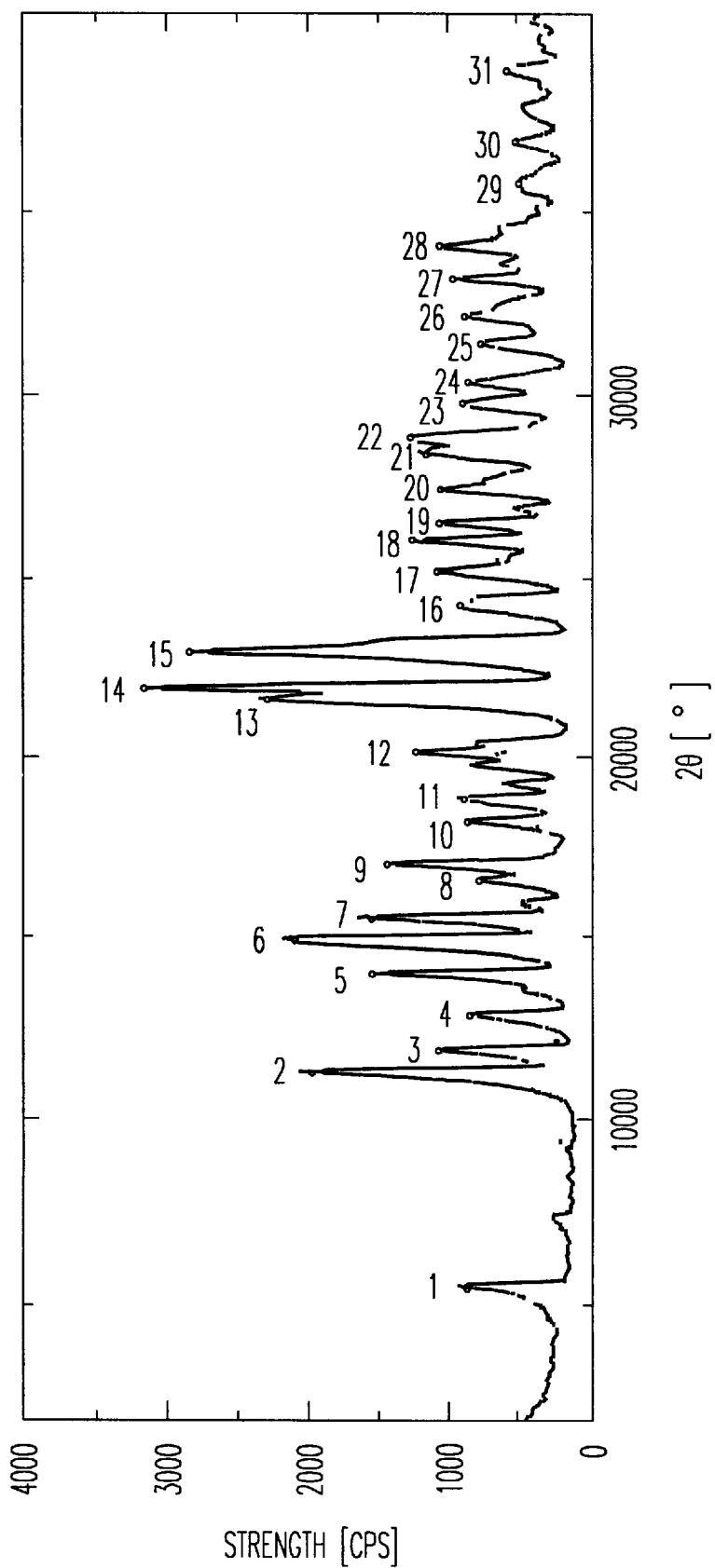
FIG. 3 shows an X-ray diffraction spectrum of crystalline dCP4U.4Na (decahydrate).
Figure 4:
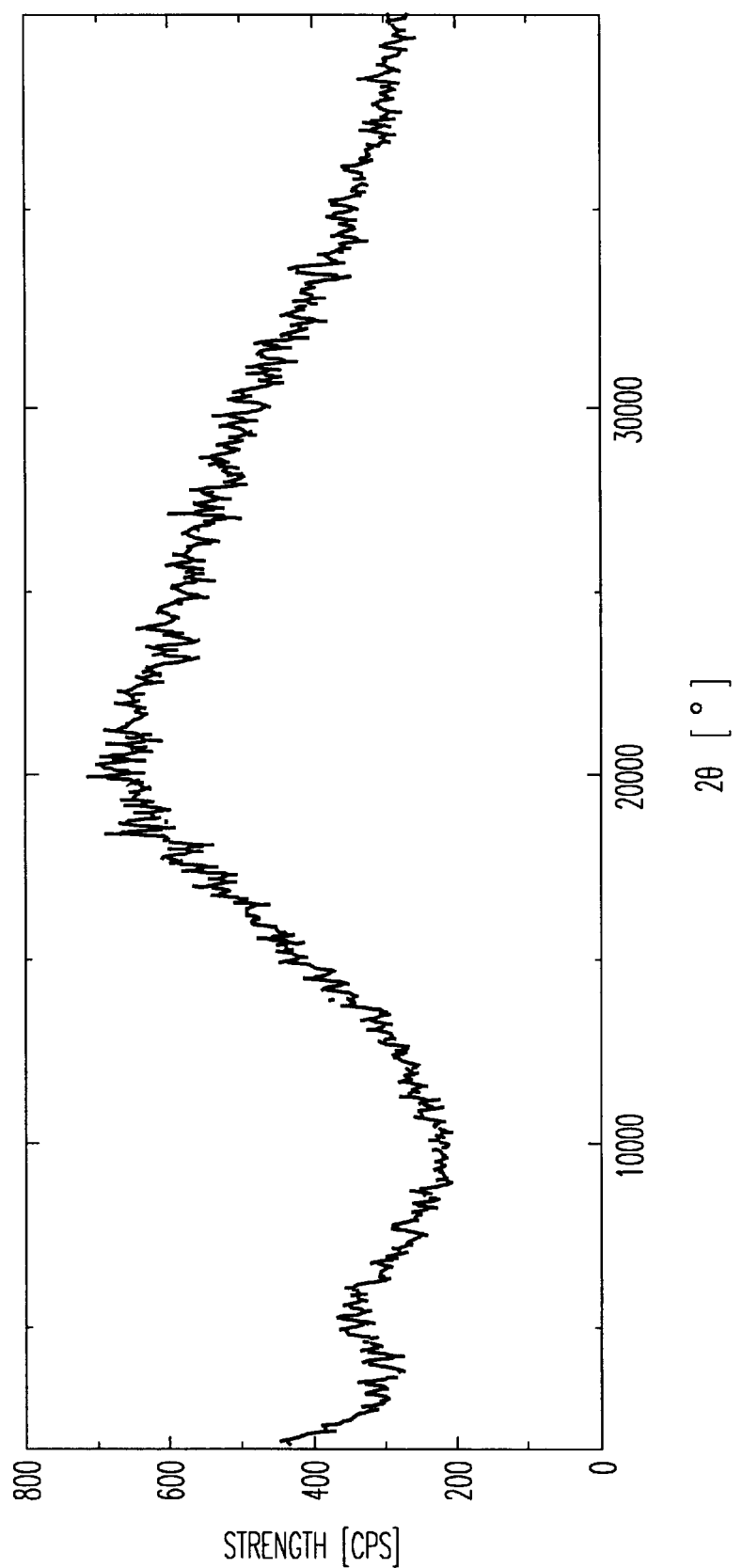
FIG. 4 shows an X-ray diffraction spectrum of white powdery dCP4U (freeze-dried product).

The dCP4U.4Na crystals were subjected to X-ray diffraction by use of an X-ray diffraction apparatus (Model: RINT2500V, product of Rigaku Denki) under the following conditions (measurement error: ±0.1°. The thus-obtained X-ray diffraction spectrum and the peak data of dCP4U·4Na 3.5-hyudrate are shown in FIG. 2 and Table 3, respectively. Similarly, the X-ray diffraction spectrum and the peak data dCP4U.4Na decahydrate are shown in FIG. 3 and Table 4, respectively. In addition, the X-ray diffraction spectrum of the freeze-dried product is shown in FIG. 4 as a reference.

(Conditions for Measurement)

X-ray tube: Cu-Kα

X-ray output: 50 kV-300 mA

Scanning rate: 4.0°/minute

Scanning interval: 0.02°

Angle measuring range: 2–40°

Slit: DS-0.5°, RS-0.15 mm, SS-0.5°

Pre-treatment: Grinding by use of an agate mortar

TABLE 3

Crystalline dCP4U · 4Na 3.5-hydrate

| Peak No. | 2θ (°) | Relative intensity |
|---|---|---|
| 1 | 6.18 | 39 |
| 2 | 8.82 | 38 |
| 3 | 11.50 | 27 |
| 4 | 12.32 | 79 |
| 5 | 13.76 | 39 |
| 6 | 14.44 | 83 |
| 8 | 16.34 | 29 |
| 9 | 16.84 | 34 |
| 10 | 17.68 | 100 |
| 11 | 19.02 | 81 |
| 12 | 19.72 | 36 |
| 13 | 20.86 | 35 |
| 14 | 22.28 | 78 |
| 15 | 23.54 | 47 |
| 16 | 25.04 | 43 |

TABLE 4

Crystalline dCP4U · 4Na decahydrate

| Peak No. | 2θ (°) | Relative intensity |
|---|---|---|
| 1 | 5.58 | 28 |
| 2 | 11.34 | 62 |
| 3 | 11.94 | 34 |
| 4 | 12.92 | 27 |
| 5 | 14.08 | 49 |
| 6 | 14.96 | 66 |
| 7 | 15.60 | 49 |
| 8 | 16.62 | 25 |
| 9 | 17.08 | 46 |
| 10 | 18.28 | 27 |
| 11 | 18.90 | 28 |
| 12 | 20.20 | 39 |
| 13 | 21.66 | 72 |
| 14 | 22.02 | 100 |
| 15 | 23.02 | 90 |

6) Hygroscopicity dCP4U.4Na crystals (decahydrate) having a water content of approximately 17.4% were allowed to stand for two days under the following conditions a), b) and c): a) 25° C. and a relative humidity of 57%; b) 25° C. and a relative humidity of 75%; c) 25° C. and a relative humidity of 93%. No decomposition or change in weight was observed in the above three cases. The crystals have proven to be stable and to have no hygroscopicity. In addition, the same crystals were allowed to stand for seven days under the following severe conditions d): d) 40° C. and a relative humidity of 75%. No change was observed in this case.

In contrast, when a freeze-dried product (initial water content: approximately 1%) was stored for two days under the following conditions b) or c): b) 25° C. and a relative humidity of 75% and c) 25° C. and a relative humidity of 93%, on the second day of storage, the product assumed a mud-like state due to gradual increase in water content.

7) Stability dCP4U.4Na crystals (decahydrate) and a freeze-dried product were individually placed in bottles, which were then sealed and stored for 13 days at 60° C. (acceleration test). No decomposition of the crystals was observed. In contrast, the freeze-dried product was found to have been partially decomposed as proven through observation of a purity loss of the product of approximately 2.2%.

7) NMR

Each of the dCP4U.4Na crystals and the freeze-dried product was directly charged into a zirconia-made rotor, and the corresponding $^{13}$C-CPMAS-NMR spectrum was measured. Conditions for measurement are described below.

$^{13}$C-CPMAS-NMR

| | | |
|---|---|---|
| 1) Apparatus | CMX-300 (product of Chemagnetics) |
| 2) Method for measurement | CPMAS (sideband suppression) |
| 3) Measurement temperature | room temperature |
| 4) Observed nucleus | $^{13}$C |
| 5) Frequency of observation | 75.502 MHz |
| 6) Pulse width of proton excitation | 4.5 μs |
| 7) Contact time | 0.5 msec. |
| 8) Measurement width | 30.03 kHz |
| 9) Points of measurement | 2048 |
| 10) Data points | 16384 |
| 11) Repetition time | 15.0 sec. (FIGS. 6 and 7) 60.0 sec. (FIG. 5) |
| 12) Chemical shift standard | hexamethylbenzene (outer standard 17.35 ppm) |
| 13) Sample rotation speed | 5 kHz |
| 14) Integration | 256 times |

Figure 5:
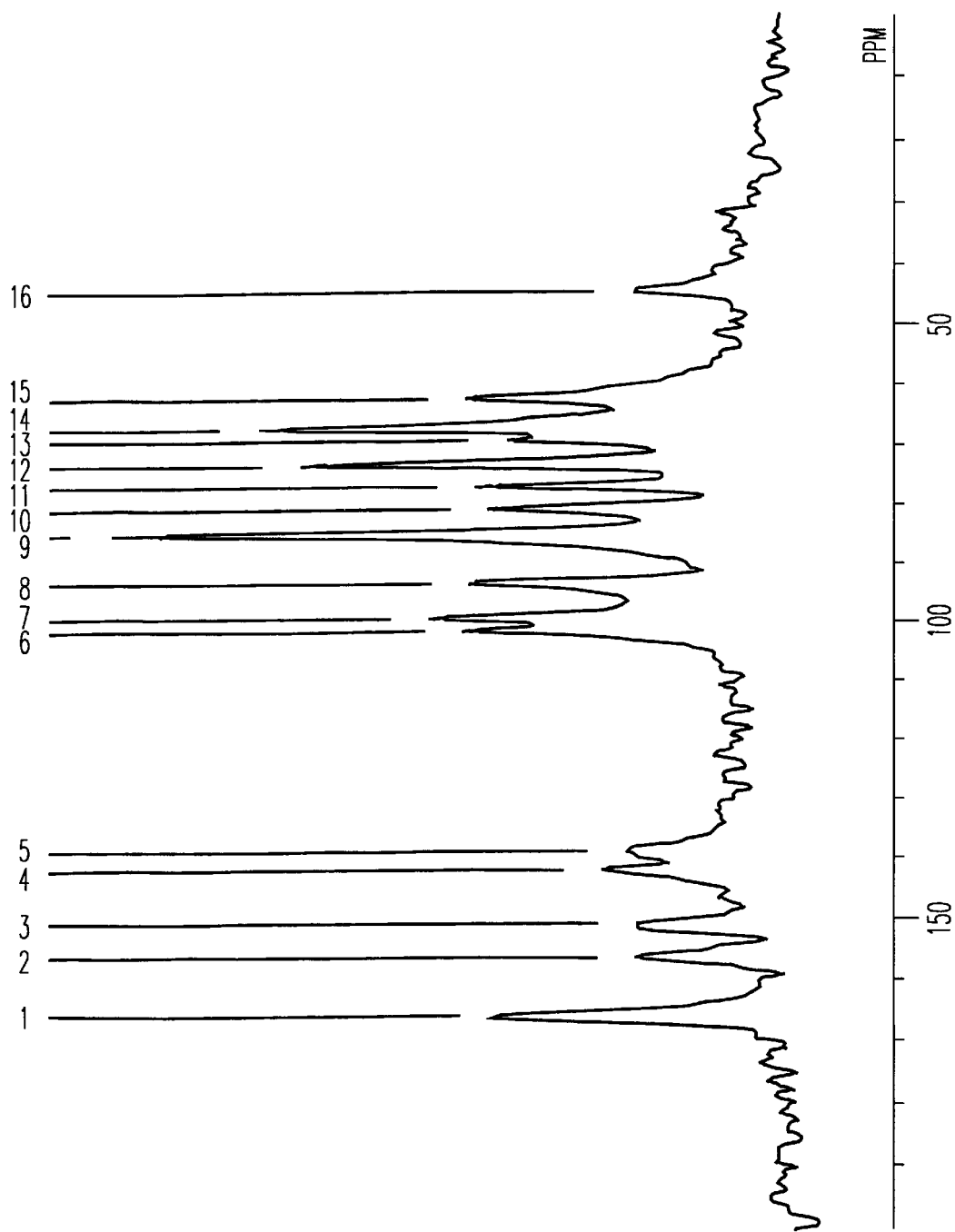
FIG. 5 shows a $^{13}$C-CPMAS-NMR spectrum of crystalline dCP4U.4Na (3.5-hydrate).
Figure 6:
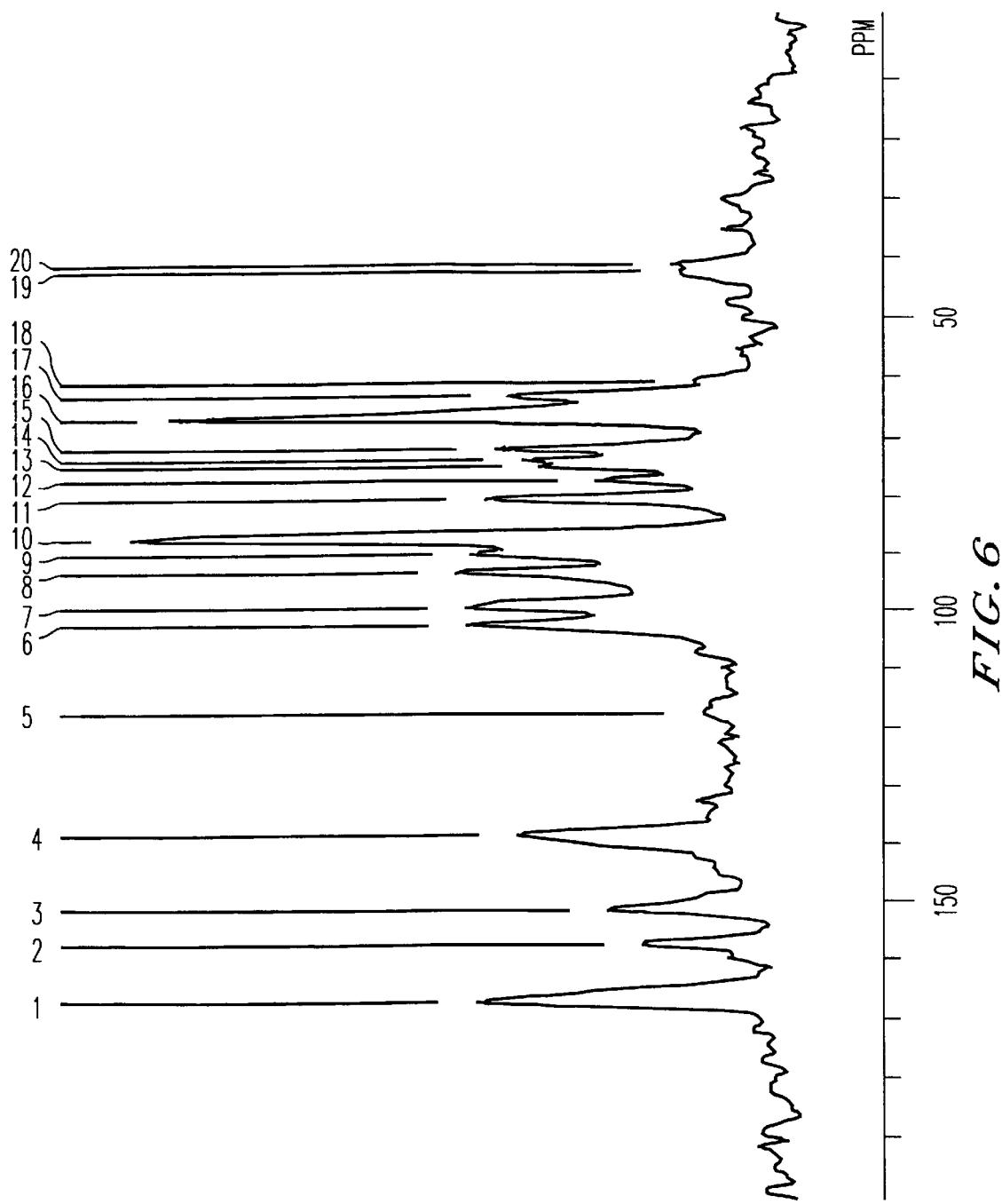
FIG. 6 shows a $^{13}$C-CPMAS-NMR spectrum of crystalline dCP4U.4Na (decahydrate).
Figure 7:
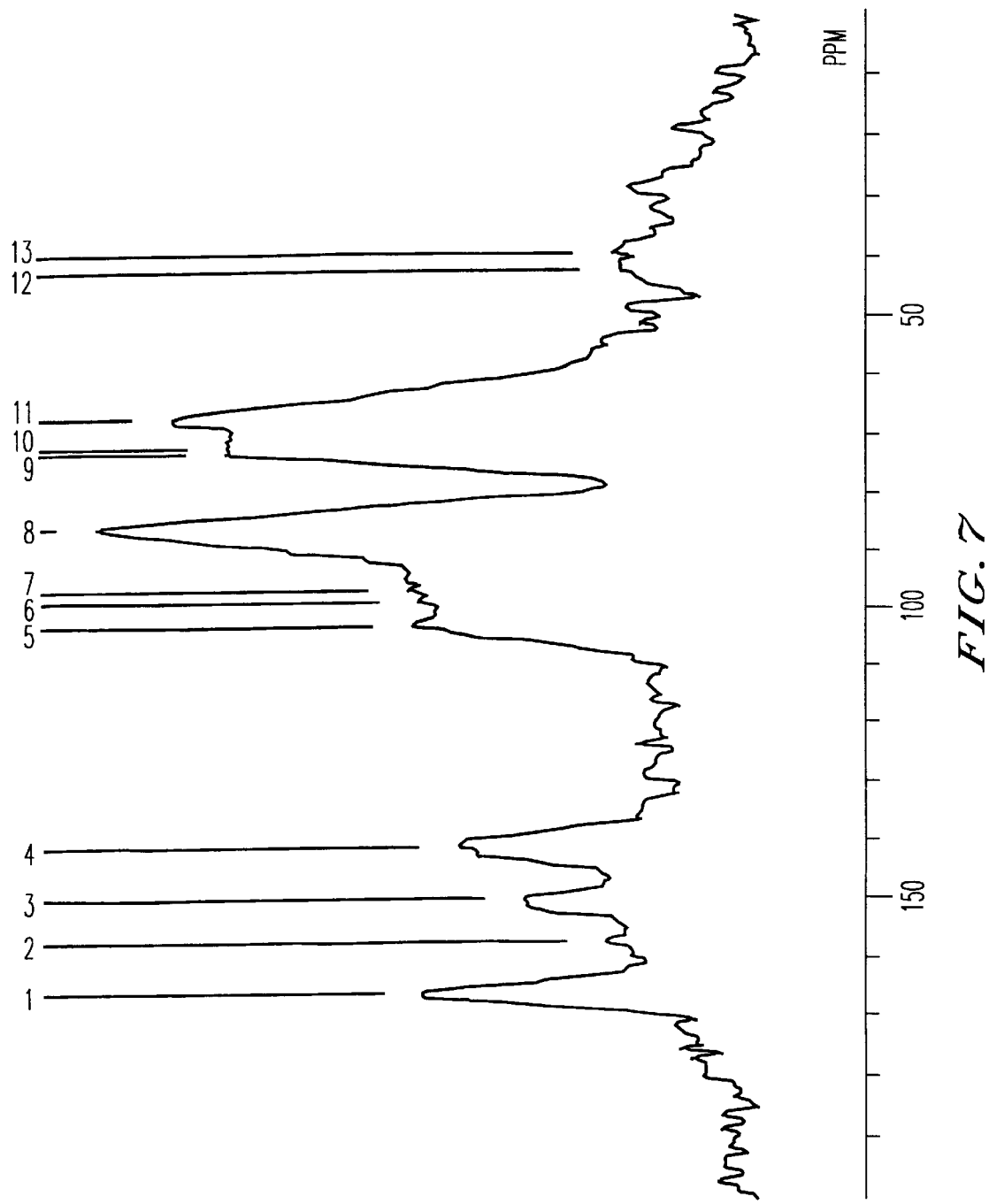
FIG. 7 shows a $^{13}$C-CPMAS-NMR spectrum of white powdery dCP4U (freeze-dried product).

FIG. 5 and Table 5 show a $^{13}$C-CPMAS-NMR spectrum of crystalline dCP4U.4Na 3.5-hydrate and the peak data, respectively. FIG. 6 and Table 6 show a $^{13}$C-CPMAS-NMR spectrum of crystalline dCP4U.4Na decahydrate and the peak data, respectively. FIG. 7 and Table 7 show a $^{13}$C-CPMAS-NMR spectrum of dCP4U in the form of white powder (freeze-dried product) and the peak data, respectively. The numerals in FIGS. 5 to 7 refer to the corresponding peak numbers in Tables 5 to 7.

TABLE 5

Crystalline dCP4U · 4Na 3.5-hydrate (ppm)

| (1) | 166.1 | (2) | 156.2 | (3) | 150.9 | (4) | 141.6 |
|---|---|---|---|---|---|---|---|
| (5) | 138.4 | (6) | 101.3 | (7) | 99.2 | (8) | 93.2 |
| (9) | 84.9 | (10) | 80.6 | (11) | 76.7 | (12) | 73.1 |
| (13) | 69.0 | (14) | 67.2 | (15) | 62.2 | (16) | 43.9 |

TABLE 6

Crystalline dCP4U · 4Na decahydrate (ppm)

| (1) | 167.4 | (2) | 157.8 | (3) | 151.6 | (4) | 139.0 |
|---|---|---|---|---|---|---|---|
| (5) | 117.9 | (6) | 102.6 | (7) | 99.3 | (8) | 93.3 |
| (9) | 90.1 | (10) | 87.3 | (11) | 80.6 | (12) | 77.2 |
| (13) | 75.0 | (14) | 73.9 | (15) | 72.0 | (16) | 67.0 |
| (17) | 63.1 | (18) | 60.4 | (19) | 42.0 | (20) | 40.8 |

TABLE 7

White powder of dCP4U (freeze-dried product) (ppm)

| (1) | 166.5 | (2) | 157.4 | (3) | 149.9 | (4) | 140.9 |
|---|---|---|---|---|---|---|---|
| (5) | 103.0 | (6) | 99.0 | (7) | 96.9 | (8) | 85.9 |
| (9) | 73.4 | (10) | 71.7 | (11) | 67.1 | (12) | 42.0 |
| (13) | 39.3 | | | | | | |

Example 2

Synthesis of dCP4U from UMP

Formamide (2.5 ml) and pyridine (7.6 ml) were added to a dehydrated triethylamine salt (10 mmol) of pyrophosphate (TEA-PPi), followed by stirring the resultant mixture. To a dehydrated tributylamine salt of uridine 5'-monophosphate (UMP-TBA) (10 mmol) placed in another vessel, DMAC (3.6 ml), dioxane (3.2 ml), and tributylamine (3.3 ml) were added and stirred, and DPC (2.3 ml) was added dropwise thereto. The mixture was stirred at room temperature for one hour, to thereby form UMP-DPP, which was added to the aforementioned dehydrated solution of TEA-PPi prepared in advance. The reaction mixture was stirred at room temperature for one hour, forming UTP. DMAC (7.2 ml) was added to a tributylamine salt of 2'-deoxycytidine 5'-monophosphate (TBA-dCMP) (4.9 g, 10 mmol) placed in another vessel, to thereby form a suspension, and DPC (2.2 ml, 1.1 equivalents) was added to the suspension. The resultant mixture was stirred for 40 minutes, and tributylamine (TBA) (9.5 ml) was added to the mixture. Another 20 minutes stirring was carrier out, to thereby prepare dCMP-DPP. The thus-prepared dCMP-DPP solution was added to the aforementioned synthesized UTP solution prepared in advance, and the mixture was stirred at room temperature for 56 hours. Reaction was terminated by adding water, and the pH of the reaction mixture was adjusted to 11 by adding a 30% aqueous sodium hydroxide solution. After the solvent was removed by concentration, the pH was adjusted to 7.0 by adding a 6 mol/L hydrochloric acid. The mixture was partitioned with ethyl acetate. The aqueous layer formed by partitioning was subjected to HPLC analysis (272 nm), revealing that the synthesis yield of dCP4U was 37.7%.

INDUSTRIAL APPLICABILITY

As described hereinabove, the crystals of dCP4U obtained through the process according to the present invention have high purity and high stability and no hygroscopicity as compared with a freeze-dried product, to thereby serve as a useful raw material for preparing a pharmaceutical.

The process for producing dCP4U according to the present invention permits use of inexpensive UMP as a raw material and realizes high yield. Thus, the process is suitable for large-scale synthesis of dCP4U.

What is claimed is:

1. A crystal of a $P^1$-(2'-deoxycytidine 5'-)$P^4$-(uridine 5'-)tetraphosphate salt.

2. A crystal of $P^1$-(2'-deoxycytidine 5'-)$P^4$-(uridine 5'-)tetraphosphate.4Na.

3. The crystal according to claim 1 or 2 having a purity of at least 95%.

4. The crystal according to claim 1 or 2 having a purity of at least 97% and containing 2% or less uridine 5'-triphosphate.

5. The crystal according to claim 1 or 2 having a purity of at least 98% and containing 1% or less uridine 5'-triphosphate.

6. A process for producing the crystal of claim 1, which process comprises subjecting crude $P^1$-(2'-deoxycytidine 5'-)$P^4$-(uridine 5'-)tetraphosphate to a purification process of anion exchange chromatography and activated-charcoal chromatography, and adding, to the resultant solution of purified $P^1$-(2'-deoxycytidine 5'-) $P^4$-(uridine 5'-)tetraphosphate, a hydrophilic organic solvent, to thereby cause precipitation of a $P^1$-(2'-deoxycytidine 5'-)$P^4$-(uridine 5'-)tetraphosphate salt in the form of crystals.

7. A process according to claim 6, wherein the purification process comprises anion exchange chromatography performed first and subsequent activated-charcoal chromatography.

8. A process for producing $P^1$-(2'-deoxycytidine 5'-)$P^4$-(uridine 5'-)tetraphosphate (dCP4U), which process comprises reacting uridine 5'-monophosphate (UMP), 2'-deoxycytidine 5'-monophosphate (dCMP), diphenyl phosphorochloridate (DPC), and a pyrophosphate (PPi), wherein UMP and DPC are reacted in a first stage, thereby forming a reaction mixture comprising UMP diphenylphosphate (UMP-DPP);

further treating the UMP-DPP-containing reaction mixture with PPi, thereby forming a mixture comprising uridine 5'-triphosphate (UTP); and reacting the thus-formed UTP, without isolation from the reaction mixture, with dCMP in the presence of DPC, thereby providing dCP4U.

9. A crystal which is a hydrate salt having 1–14 molecules of water which are bound to or adhere to one molecule of the $P^1$-(2'-deoxycytidine 5'-)-$P^4$-(uridine 5'-)tetraphosphate salt.

10. The crystal according to claim 9 having a purity of at least 98% and containing 1% or less uridine 5'-triphosphate.

11. The crystal of claim 9 having 3.5 molecules of water which are bound to or adhere to one molecule of the $P^1$-(2'-deoxycytidine 5'-)-$P^4$-(uridine 5'-)tetraphosphate salt.

12. The crystal of claim 9 having 10 molecules of water which are bound to or adhere to one molecule of the $P^1$-(2'-deoxycytidine 5'-)-$P^4$-(uridine 5'-)tetraphosphate salt.

13. The crystal according to claim 9 having a purity of at least 95%.

14. The crystal according to claim 9 having a purity of at 97% and containing 2% or less uridine 5'-triphosphate.

* * * * *